US006191162B1

(12) United States Patent
Byrd et al.

(10) Patent No.: US 6,191,162 B1
(45) Date of Patent: Feb. 20, 2001

(54) METHOD OF REDUCING SERUM GLUCOSE LEVELS

(75) Inventors: Edward A. Byrd, San Francisco, CA (US); Rajiv Janjikhel, Owings Mills, MD (US)

(73) Assignee: Medical Research Institute, San Bruno, CA (US)

( * ) Notice: Under 35 U.S.C. 154(b), the term of this patent shall be extended for 0 days.

(21) Appl. No.: 09/288,253

(22) Filed: Apr. 8, 1999

Related U.S. Application Data

(63) Continuation-in-part of application No. 09/112,623, filed on Jul. 9, 1998

(60) Provisional application No. 60/102,605, filed on Oct. 1, 1998, and provisional application No. 60/087,203, filed on May 28, 1998.

(51) Int. Cl.$^7$ .................................................. A61K 31/385
(52) U.S. Cl. ............................................. 514/440; 514/866
(58) Field of Search ....................................... 514/440, 866

(56) References Cited

U.S. PATENT DOCUMENTS

| | | | |
|---|---|---|---|
| 3,577,551 | 5/1971 | Murakami et al. | 424/325 |
| 4,705,867 | 11/1987 | Giray et al. | 549/39 |
| 4,800,044 | 1/1989 | Giray et al. | 260/399 |
| 4,966,732 | 10/1990 | Giray et al. | 260/399 |
| 5,334,612 | 8/1994 | Kalden et al. | 514/440 |
| 5,376,382 | 12/1994 | Goede et al. | 424/464 |
| 5,455,264 | 10/1995 | Beisswenger et al. | 514/440 |
| 5,527,539 | 6/1996 | Sarlikiotis et al. | 424/464 |
| 5,532,269 | 7/1996 | Koltringer | 514/440 |
| 5,569,670 | 10/1996 | Weischer et al. | 514/440 |
| 5,599,835 | 2/1997 | Fischer | 514/440 |
| 5,650,429 | 7/1997 | Conrad et al. | 514/440 |
| 5,691,379 | 11/1997 | Ulrich et al. | 514/557 |
| 5,693,664 | 12/1997 | Wessel et al. | 514/440 |
| 5,705,192 | 1/1998 | Bethge et al. | 424/489 |
| 5,728,735 | 3/1998 | Ulrich et al. | 514/560 |
| 5,730,988 | 3/1998 | Womack | 424/195.1 |
| 5,827,643 | 10/1998 | Conrad et al. | 435/2 |

FOREIGN PATENT DOCUMENTS

| | | |
|---|---|---|
| 1 668 887 | 7/1971 | (DE) . |
| 36 29 116 A1 | 3/1988 | (DE) . |
| 42 20 851 A1 | 1/1993 | (DE) . |
| 43 17 646 A1 | 12/1994 | (DE) . |
| 43 38 508 A1 | 5/1995 | (DE) . |
| 43 43 592 A1 | 6/1995 | (DE) . |
| 43 43 647 A1 | 6/1995 | (DE) . |
| 44 00 269 A1 | 7/1995 | (DE) . |
| 44 47 599 A1 | 7/1996 | (DE) . |
| 0 159 519 | 2/1987 | (EP) . |
| 0 702 953 A2 | 8/1995 | (EP) . |
| 0 733 363 A1 | 3/1996 | (EP) . |
| 0 712 574 A2 | 10/1996 | (EP) . |
| 60-184011 | 9/1985 | (JP) . |
| WO 98/57627 | 12/1998 | (WO) . |

OTHER PUBLICATIONS

Armstrong et al., *Free Radical Biology and Chemistry,* (1996) 21(5):719–726.
Barbiroli et al., *J Neurol,* (1995) 242:472–477.
Baur et al., *Klin Wochenschr,* (1991) 69:722–724.
Bilich et al., *I–Pharmacodynamics,* (1978) 88:93.
Black et al., *Clinical and Experimental Pharmacology and Physiology,* (1998) 25:712–714.
Bloomgarden, *Diabetes Care,* (Apr. 1997) 20(4):670–673.
Burkart et al., *Agents Actions,* (1993) 38:60–65.
Busse et al., *Arzneim–Forsch/Drug Research* (1992) 42(6):829–831.
Bustamante et al., *Free Radical Biology and Medicine,* (1998) 24(6):1023–1039.
Carreau, *Methods in Enzymology,* (1979) 62:152–158.
Cesolari et al., *Rev Exp Enf Ap Digest,* (1988) 73(3) 229–232.
Chen et al., *Archives of Biochemistry and Biophysics,* (1997) 338(2):165–172.
Devasgayam et al., *Chem–Biol Interactions,* (1993) 86:79–92.
Dimpfel et al., *Dev Pharmacol Ther,* (1990) 14:193–199.
Egan et al., *Prostaglandins,* (1978) 16)6):861–869.
Estrada et al., *Diabetes,* (Dec. 1996) 45:1798–1804.
Faust et al., *J. Immunopharmac,* (1994) 16(1):61–66.
Fuchs et al., *Skin Pharmacol,* (1994) 7:278–284.
Gandhi et al., *J Biosci,* (Sep. 1985) 9 (1 & 2):117–127.
Garrett et al., *Neuroscience Letters,* (1997) 222:191–194.
Gerbitz et al., *Diabetes,* (Feb. 1996) 45:113–126.
Hammarqvist et al., *Crit Care Med,* (1997) 25(1):78–84.
Haugaard et al., *Biochem Biophys Acta,* (1970) 222:583–586.
Henricksen et al., *American Physiological Society,* (1990) C648–C653.
Henricksen et al., *Life Sciences,* (1997) 61(8):805–812.
Hofmann et al., *Archives of Biochemistry and Biophysics,* (1995) 324(1):85–92.
Jacob et al., *Diabetes,* (1995) 245–250.
Jacob et al., *Diabetes,* (Aug. 1996) 45:1024–1029.

(List continued on next page.)

*Primary Examiner*—Theodore J. Criares
*Assistant Examiner*—Jennifer Kim
(74) *Attorney, Agent, or Firm*—Karl Bozicevic; Bozicevic, Field, Francis LLP

(57) ABSTRACT

A controlled release formulation of lipoic acid is administered to a patient resulting in reduced serum glucose levels. The formulation comprises a pharmaceutically acceptable carrier and is designed to prevent degradation of the lipoic acid in the gastrointestinal tract and to release the lipoic acid in a controlled manner thereby obtaining a desired lipoic acid serum level over an extended period resulting in reduced serum glucose levels over that period.

14 Claims, No Drawings

OTHER PUBLICATIONS

Kagan et al., *Biochemical Pharmacology*, (1992) 44(8):1637–1649.
Kagan et al., *Journal of Lipid Research*, (1992) 33:385–397.
Kagan, et al., *Free Rad Res Comms*, (1991) 15(5):265–276.
Khamaisi et al., *Metabolism*, (Jul. 1997) 45(7):763–768.
Lavis et al., *The Journal of Biologic Chemistry*, (Jan. 10, 1970) 245(1):23–31.
Lodge et al., *Journal of Applied Nutrition*, (1997) 49 (1 & 2)3–11.
Lodge et al., *Free Radical Biology & Medicine*, (1998) 25(3):287–297.
Matsugo et al., *Biochemistry and Molecular Biology International*, (Oct. 1995) 37(2)375–383.
Merin et al., *FEBS Letters*, (1996) 294:9–13.
Muller et al., *Toxicology*, (1989) 58:175–185.
Muller et al., *Biochimica et Biophysica Acta*, (1990) 1052:386–389.
Muller et al., *Journal of Cerebral Blood Flow and Metabolism*, (1995) 15:624–630.
Nagamatsu et al., *Diabetes Care*, (1995) 18(8):1160–1167.
National Diabetes Data Group Classification and Diagnosis of Diabetes Mellitus and Other Categories of Glucose Intolerance, *Diabetes* (1979) 28:1039–1057.
Natraj et al., *J. Biosci*, (1984) 6(1):38–46.
Nickander et al., *Free Radical Biology & Medicine* (1996) 21(5):631–639.
Ohmori et al., *Japan J. Pharmacol*, (1986) 42:275–280.
Ohmori et al., *Japan J. Pharmacol*, (1986) 42:135–140.
Ou et al., *Free Rad Res*, (1996) 25(4):337–346.
Ou et al., *Biochemial Pharmacology*, (1995) 50(1):123–126.
Packer et al., *Free Radical Biology & Medicine*, (1997) 22(1/2):359–378.
Packer et al., *Free Radical Biology & Medicine*, (1995) 19(2):227–250.
Packer, *Diabetologica*, (1993) 36:1212–1213.
Pascoe et al., *Free Radical Biology & Medicine*, (1989) 6:209–224.
Peinado et al., *Archives of Biochemistry and Biophysics*, (Sep. 1989) 273(2):389–395.
Podda et al., *Biochemical Pharmacology*, (1996) 52:627–633.
Prehn et al., *Journal of Cerebral Blood Flow and Metabolism* (1992) 12:78–87.
Reed et al., *Science*, (1951) 93–94.
Roy et al., *Biochemical Pharmacology*, (1997) 53:393–399.
Scheer et al., *Archives of Biochemistry and Biophysics*, (May 1, 1993) 302(2):385–390.
Schmid et al., *FASEB Journal*, (Jul. 1998) 12:863–870.
Schonheit et al., *Biochimica et Biophysica Acta*, (1995) 1271:335–342.
Segermann et al., *Arzneim.–Forsch./Drug Res.*, (1991) 41(12):1294–1298.
Sen et al., *The FASEB Journal*, (May 1996) 10:709–720.
Sen et al., *Free Radical Biology & Medicine*, (1997) 22(7):1241–1257.
Sen et al., *Biochemical and Biophysical Research Communications* (1998) 247:223–228.
Simopoulos, *Nutrition Today*, (Jan./Feb. 1994) 12–16.
Stoll et al., *Pharmacology Biochemistry and Behavior*, (1993) 46:799–805.
Streeper et al., *American Physiological Society*, (1997) 273(1):E185–E191.
Sumathi et al., *Jpn J Med Sci Biol*, (1996) 49:39–48.
Suzuki et al., *Free Rad Res Commsii*, (1992) 17(3):211–217.
Suzuki et al., *Biochemical and Biophysical Research Communications,*, (Dec. 1992) 189(3):1709–1715.
Suzuki et al., *Free Rad Res Comms*, (1991) 15(5) 255–263.
Szabo et al., *Klin Wochenschr*, (1986) 64(Suppl. VII):116–122.
Teichert et al., *Methods in Enzymology*, (1997) vol. 279.
Wagh et al., *J. Biosci*, (Mar. 1987) 11(1):59–74.
Wagh et al., *J. Biosci*, (Jun. 1986) 10(2):171–179.
Wagner et al., *Properties and Derivatives of α–Lipoic Acid*, (Oct. 5, 1956) 5079–5081.
Wickramasinghe et al., *Biochemical Pharmacology*, (1992) 43(3) 407–411.
Witt et al., *Journal of Chromatography B*, (1998) 705:127–131.
Wolz et al., *Neruopharmacology*, (1996) 35(3):369–375.
Ziegler et al., *Deutsche Medizinische Wochenschritt*, (Jul. 1, 1988) 113(26) 1071–1074.
Ziegler et al., *Diabetologia*, (1995) 38:1425–1433.
Zimmer et al., *J Mol Cell Cardiol*, (1995) 27:1895–1903.

METHOD OF REDUCING SERUM GLUCOSE LEVELS

This application is a continuation-in-part of earlier filed provisional application Serial No. 60/102,605, filed Oct. 1, 1998 and patent application Ser. No. 09/112,623, filed Jul. 9, 1998, which is converted patent application of provisional patent application Serial No. 60/087,203, filed May 28, 1998 to which we claim priority under 35 U.S.C. §120 and §119(e) each of which is incorporated herein by reference in their entirety.

FIELD OF THE INVENTION

This invention relates to a method of reducing serum glucose levels. More particularly, the invention relates to the administration of controlled release formulations of lipoic acid to reduce a human patients' glucose levels.

BACKGROUND OF THE INVENTION

The compound α-lipoic acid was first isolated by Reed and coworkers as an acetate replacing factor. It is assumed to be substantially insoluble in water, but soluble in organic solvents. α-lipoic acid is a chiral molecule and is known by a variety of names, including thioctic acid; 1,2-diethylene-3 pentanoic acid; 1,2-diethylene-3 valeric acid; and 6,8-thioctic acid. See Gerreke Biewenga et a., *An Overview of Lipoate Chemistry*, Lipoic Acid in Health and Disease 1 (1997) (Marcel Dekker). This document, and all other documents cited to herein, is incorporated by reference as if reproduced fully herein.

After being isolated α-lipoic acid was tentatively classified as a vitamin, but it was later found to be synthesized by animals and humans. The complete enzyme pathway that is responsible for the de novo synthesis has not yet been definitively elucidated. Several studies indicate that octanoate serves as the immediate precursor for the 8-carbon fatty acid chain, and cysteine appears to be the source of sulfur. As a lipoamide, it functions as a cofactor in the multienzyme complexes that catalyze the oxidative decarboxylation of α-keto acids such as pyruvate, α-keto glutarate, and branched chain α-keto acids.

More recently, a great deal of attention has been given to possible antioxidant functions for α-lipoic acid, and its reduced form, dihydrolipoic acid (DHLA). Lipoate, or its reduced form, DHLA, reacts with reactive oxygen species such as superoxide radicals, hydroxyl radicals, hypochlorous acid, peroxyl radicals, and singlet oxygen. It also protects membranes by interacting with vitamin C and glutathione, which may in turn recycle vitamin E. In addition to its antioxidant activities, DHLA may exert prooxidant actions to reduction of iron.

The administration of α-lipoic acid has been shown to be beneficial in a number of oxidative stress models such as ischemia-repercussion injury, diabetes (both α-lipoic acid and DHLA exhibit hydrophobic binding to proteins such as albumin, which can prevent glycation reactions), cataract formation, HIV activation, neurodegeneration, and radiation injury. Furthermore, lipoate can function as a redox regulator of proteins such as myoglobin, prolactin, thioredoxin, and NF-κB transcription factor.

Lipoate may also have other activities. For example, DHLA has been found in vitro to be an anti-inflammatory agent which at the same time interferes with nitric oxide release from inflammatory macrophages and protects target cells from oxygen radical attack. V. Burkhart, *Dihydrolipoic Acid Protects Pancreatic Islet Cells from Inflammatory Attack*, Agents Actions 38:60 (1993).

Lipoic acid is a coenzyme for several enzymes. Lipoic acid is a coenzyme for both α-keto acid dehydrogenase complex enzymes (i.e. pyruvate dehydrogenase complex and α-keto glutarate dehydrogenase complex), branched chain α-keto acid dehydrogenase complex, and the glycine cleavage system. In the enzyme system, the body forms a multi-enzyme complex involving lipoic acid, that breaks down molecules of pyruvate produced in earlier metabolism, to form slightly smaller high energy molecules called acetyl-coenzyme A. This results in molecules that can enter into a series of reactions called the citric acid cycle, or Krebs cycle, which finishes the conversion of food into energy. Essentially, lipoic acid stimulates basal glucose transport and has a positive effect on insulin stimulated glucose uptake.

SUMMARY OF THE INVENTION

A method of reducing a patient's serum glucose level via the oral administration of an active ingredient is disclosed. The active ingredient is lipoic acid, or a pharmaceutically acceptable salt, amide, ester or metabolite thereof. The active ingredient is formulated so that (1) it is not degraded in the stomach and (2) is released in the intestines at a controlled rate so that it enters the circulatory system gradually and continuously over time thereby maintaining a constant effect on suppressing serum glucose levels.

An aspect of the invention is a method of treating human patients by the oral administration of lipoic acid.

An advantage of the invention is that undesirable effects of elevated glucose levels can be suppressed.

A feature of the invention is that lipoic acid is formulated with excipient materials which result in a useful oral dosage form.

An object of the invention is to reduce a patient's glucose level over time and thereby treat insulin resistance.

An aspect of the method of the invention is that relatively low blood serum levels of lipoic acid are maintained over long periods (e.g. 6 hours or more, preferably 12 hours or more per day) each day for months or years to suppress blood serum glucose levels over those periods.

A feature of the invention is that lower blood serum levels of lipoic acid (over longer periods) are obtained as compared to single dose injectables and unformulated oral formulations of lipoic acid.

These and other objects, aspects, advantages, and features of the invention will become apparent to those persons skilled in the art upon reading the details of the methodology as more fully described below.

DETAILED DESCRIPTION OF THE INVENTION

Before the present, methods of treatment, formulations and components used therein are disclosed and described, it is to be understood that this invention is not limited to particular methods, formulations or components as such may, of course vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

The publications discussed herein are provided solely for their disclosure prior to the filing date of the present application. Nothing herein is to be construed as an admission that the present invention is not entitled to antedate such publication by virtue of prior invention. Further, the dates of publication provided are subject to change if it is found that the actual date of publication is different from that provided here.

Definitions

The term "lipoic acid" is intended to mean α-lipoic acid which is a chiral molecule also known as thioctic acid; 1,2-diethylene-3 pentanoic acid; 1,2-diethylene-3 valeric acid; and 6,8-thioctic acid. Unless specified the term covers the racemic mixture as well as any other (non-50/50) mixture of the enantiomers including substantially pure forms of either the R-(+) or the S-(−) enantiomer. Further, unless specified otherwise the term covers pharmaceutically acceptable salts (e.g. Na and K salts) and amides, esters and metabolites of the acid. The molecule formula is $C_8H_{14}O_2S_2$ the molecular weight is 206.32 and it has a pKa of 4.7. In referring to pharmaceutically acceptable salts the term is intended to encompass a conventional term of pharmaceutically acceptable acid addition salts which refer to salts which retain the biological effectiveness and properties of the free-base form of the acid and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malconic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. The same is true with respect to amides, esters and metabolites that is those forms which can be formed and maintain biological effectiveness and not have significant undesirable biological properties.

The term "excipient material" is intended to mean any compound forming a part of the formulation which is intended to act merely as a carrier i.e. not intended to have biological activity itself.

The term "chemical degradation" is intended to mean that the lipoic acid active ingredient is subjected to a chemical reaction which disrupts its biological activity.

The terms "treating", and "treatment" and the like are used herein to generally mean obtaining a desired pharmacological and physiological effect. The effect may be prophylactic in terms of preventing or partially preventing a disease, symptom or condition thereof and/or may be therapeutic in terms of a partial or complete cure of a disease, condition, symptom or adverse effect attributed to the disease. The term "treatment" as used herein covers any treatment of a disease in a mammal, particularly a human, and includes: (a) preventing the disease from occurring in a subject which may be predisposed to the disease but has not yet been diagnosed as having it; (b) inhibiting the disease, i.e. arresting it's development; or (c) relieving the disease, i.e. causing regression of the disease and/or it's symptoms or conditions. The invention is directed towards treating patient's suffering from disease related abnormally high levels of glucose and are related to the effects of free radicals and/or oxidizing agents over long periods of time. The present invention is involved in preventing, inhibiting, or relieving adverse effects attributed to high levels of serum glucose over long periods of time and/or are such caused by free radicals or oxidizing agents present in a biological system over long periods of time.

The terms "synergistic", "synergistic effect" and the like are used interchangeably herein to describe improved treatment effects obtained by combining controlled release lipoic acid formulations of the invention with one or more other orally effective diabetic compounds. Although a synergistic effect in some fields means an effect which is more than additive (e.g., one plus one equals three) in the field of treating diabetes and related diseases an additive (one plus one equals two) or less than additive (one plus one equals 1.6) effect may be synergistic. For example, if a patient has an abnormally high glucose level, e.g. 400 mg/dl, that patient's glucose level might be reduced to 300 mg/dl by the conventional orally effective antidiabetic compound. Further, at a different time the same patient with a glucose level of 400 mg/dl might be administered a different orally effective antidiabetic compound which compound reduced the patient's glucose levels from 400 to 300 mg/dl. However, if both orally effective antidiabetic compounds are administered to the patient one would not ordinarily expect an additive effect thereby obtaining a reduction to 200 mg/dl and may obtain no more of a reduction in glucose level than when either drug is administered by itself. If additive effects could always be obtained then diabetes could be readily treated in all instances by coadministering several different types of orally effective antidiabetic compounds. However, such has not been found to be an effective treatment. However, any connection with the present invention coadministration of formulations of controlled release lipoic acid of the invention can be coadministered with other orally effective antidiabetic compounds in order to improve the effects which are synergistic, i.e. greater than the effects obtained by the administration of either composition by itself.

Reducing Serum Glucose Levels

Patient's are treated by the administration of an active ingredient from a controlled release formulation. The active ingredient is lipoic acid which term includes any pharmaceutically acceptable salt, amide, ester or metabolite thereof. The active ingredient is delivered to the patient's circulatory system at a rate so that the active ingredient is maintained for four hours or more (for weeks or months) in the blood serum within a desired therapeutic range. By keeping the active ingredient within a relatively low blood serum concentration range over significant periods of time serum glucose levels are reduced over the same periods. By maintaining lower glucose levels over significant periods of time a range of beneficial effects are obtained. Stated differently, by reducing serum glucose levels from abnormally high levels a range of adverse effects caused by high glucose levels over time are avoided. These adverse effects are avoided by slowly and continuously releasing lipoic acid into the circulatory system and maintaining a lipoic acid blood serum level which is below that obtained with immediate release dosage formulations.

Method in General

In a general sense the method of the invention does not involve any particular mode of administration. However, the specific examples described here and the results obtained were obtained using controlled release oral formulations. The general concept of the invention relates to gradually administering relatively small amounts of lipoic acid to a patient's circulatory system over a period of four hours or more per day, preferably eight hours or more per day, and more preferably twelve hours or more per day. This gradual release of lipoic acid into the patient's circulatory system results in a low lipoic acid blood serum level being maintained at a constant level over a period of time. By maintaining a relatively low level of lipoic acid in the patient's blood serum over many hours per day a number of improved unexpected results were obtained in terms of continually reducing a patient's serum glucose level and thereby avoiding the negative effects by higher serum glucose levels. In order to realize some of the more important advantages of the invention and the low level of lipoic acid in the patient's blood serum are preferably maintained repeatedly over a number of days, weeks, months or even years. Thus, in a basic sense the invention involves maintaining a substantially constant lipoic acid blood serum level in a patient over a period of four hours or more, preferably eight hours or more, and more preferably twelve hours or more per day and then repeatedly maintaining that level over a period of three days or more. Preferably, the lipoic acid blood serum levels are maintained over a week or more, more preferably a month or more and still more preferably a year or more thereby obtaining a number of advantages or, stated differently, avoiding a number of adverse effects caused by elevated serum glucose levels.

In a very specific sense the invention involves obtaining a lipoic acid blood serum level in a human patient in a range of from about 25 to about 75 ng/ml of plasma, preferably about 35 to about 65 ng/ml of plasma and more preferably about 50 ng/ml plasma ±5%. These lipoic acid blood serum levels are substantially below the levels obtained with single dose injectables or with unformulated lipoic acid oral formulations which immediately release all of the active ingredient. Thus, the method of the present invention maintains lower levels of lipoic acid in the patient's blood serum but maintains such over substantially longer periods of time.

Active Ingredient—Lipoic Acid

Various types of lipoic acids may be used in the practice of the invention. α-lipoic acid is a chiral molecule, and is discussed generally in Lipoic Acid in Health and Disease 337 (1997) (Marcel Dekker). α-lipoic acid may be obtained according to conventional syntheses, such as those disclosed in the U.S. Patents to Sutherland et al. (U.S. Pat. No. 4,772,727), Giray et al. (U.S. Pat. No. 4,966,732), Paust et al. (U.S. Pat. No. 5,380,920), and Paust et al. (U.S. Pat. No. 5,489,694).

α-lipoic acid occurs in two enantiomeric forms. The first form, R-(+)-α-lipoic acid is a physiologically occurring enantiomer. The other enantiomer, S-(−)-α-lipoic acid, may also have some physiologic activity. Discussion of the pharmacokinetics of these two enantiomers may be found in Robert Hermann et al., *Human Pharmacokinetics of α-Lipoic Acid*, Lipoic Acid in Health and Disease 337 (1997) (Marcel Dekker).

Mixtures of the two enantiomers may be used in the practice of the invention. For example, a 50/50 racemic mixture may be used in the practice of the invention. Alternatively, other ratios may also be used in the practice of the invention. For example, a 70/30 ratio of R-(+) to S-(−)-α-lipoic acid may be used, if desired. The invention may be practiced with either of the two enantiomers or in any combination thereof In a preferable embodiment, the concentration of R-(+)-α-lipoic acid ranges from about one to about seventy weight percent, based on the total weight. In another preferable embodiment, the concentration of S-(−)-α-lipoic acid ranges from one to about seventy weight percent, based on the total weight. In yet another preferable embodiment, the α-lipoic acid comprises a mixture of R-(+)-α-lipoic acid and S-(−)-α-lipoic acid, and the ratio of R-(+)-α-lipoic acid to S-(−)-α-lipoic acid ranges from about 90:10 to about 10:90, respectively based on weight.

In some cases, it may be appropriate to administer lipoic acid in the form of its therapeutically acceptable salts. These salts may be prepared in the conventional manner.

Salt formers that may, for example, be used are conventional bases or cations which are physiologically acceptable in the salt form. Examples thereof are: alkali metals or alkaline earth metals, ammonium hydroxide, basic amino acids such as arginine and lysine, amines of formula NR1R2R3 where the radicals R1, R2 and R3 are the same or different and represent hydrogen, C1–C4-alkyl or C1–C4 oxyalkyl such as mono- and diethanol-amine, 1-amino-2-propanol, 3-amino-1-propanol; alkylene diamines having one alkylene chain composed of 2 to 6 carbon atoms such as ethylene diamine or hexamethylene tetramine, and saturated cyclic amino compounds with 4–6 cyclic carbon atmos such as piperidine, piperazine, pyrrolidine, morpholine; N-methyl glucamine, creatine, or tromethamine.

Should lipoic acid be used in the form of its salts, the salt former may also be used in excess, i.e. in an amount greater than equimolar.

Additionally, lipoic acid. i.e. lipoate, may be taken to mean, within the context of the invention, to include various analogs, prodrugs, various oxidation states of the fundamental lipoic acid molecule, metabolites, and salts of any of the above. For example, included might be dihydrolipoic acid, beta-lipoic acid, the thiosulfonate of lipoic acid and a sodium salt of lipoic acid. Such lipoic acids may be administered to a mammal.

Formulation in General

The formulation used in the method of the invention is preferably an oral dosage formulation which may be in any suitable oral form including tablets, capsules, caplets, suspensions, etc. The dosage may be of any desired size in terms of the lipoic acid active ingredient. However, sizes in a range of about 50 mg to about 1,000 mg are generally used, preferably 100 mg to 500 mg and more preferably about 300 mg. The amount a patient will need to obtain an optimum therapeutical effect will vary with a number of factors known to those skilled in the art e.g. the size, age, weight, sex and condition of the patient. The patient may begin with daily doses of about 300 mg and determine if glucose levels are reduced to acceptable levels. If the desired results are not obtained in one week the daily dosage amount can be increased in increments of 100 to 300 mg/day up to any useful amount e.g. 2,000 mg/day.

The manufactured compound α-lipoic generally exists as a 50/50 or racemic mixture of R-(+)-α-lipoic acid and S-(−)-α-lipoic acid. The R-(+) enantiomer is the naturally produced biological form of the compound and as such is believed to be largely responsible for obtaining the physiological effect. Thus, the active ingredient of the formulation of the present invention may be 100% R-(+) enantiomer. However, the active ingredient may be present in any mix of the two enantiomers e.g. 10% S-(−) and 90% R-(+); 25%

S-(−) and 75% R-(+). Further, it should be noted that even though the R-(+) enantiomer is believed to be the more active the S-(−) enantiomer may possess unique properties which make inclusion of the S-(−) enantiomer important in any formulation used in treatment. Unless stated otherwise information disclosed here refers to formulations containing a racemic mixture. If the active ingredient is not a racemic mixture then some adjustment may be needed in the formulation in order to account for the greater activity of the R-(+) enantiomer as well as the slightly longer half life of the R-(+) enantiomer compared to the S-(−) enantiomer.

A typical formulation contains about 50–70% by weight lipoic acid active ingredient with the remainder being excipient material. Preferably the formulation comprises 55% to 65% active ingredient and more preferably about 60% active ingredient by weight. Thus, a particularly preferred oral formulation of the invention comprises about 300 mg of lipoic acid and about 200 mg of excipient material. Human patients generally eat during the day and sleep at night. Eating causes increased glucose levels. Accordingly, it is generally preferable to give a larger dose of lipoic acid at the beginning of the day. This may include two 300 mg tablets or a single 600 mg tablet. Later in the day the patient will take an additional 300 mg for a typical daily dose of about 900 mg for a 70 kg man.

The formulation is characterized by (a) protecting the active ingredient from chemical degradation in a patient's gastrointestinal tract and (b) releasing the active ingredient in a controlled manner. By gradually releasing the active ingredient the serum levels of lipoic acid obtained are (1) lower than those obtained with single dose injectable or a non-controlled release formulation; and (2) maintained over longer periods of time than obtained with single dose injectable or a non-controlled release formulation. Specifically, a formulation of the invention releases active ingredient so as to obtain a blood serum level in a human patient in a range of about 25 to 75 ng/ml of plasma. The range is preferably about 35 to 65 ng/ml of plasma and more preferably about 50 ng/ml of plasma ±5%.

One aspect of the invention is that a range of highly desirable therapeutic effects are obtained even when the lipoic acid blood serum levels are maintained in a range well below those previous used. The present invention could obtain desired therapeutics effects with higher levels of lipoic acid in blood serum. However, at least minimum levels would need to be constantly maintained over a long period of time (4 hours or more per day) for a plurality of days to obtain the desired results.

The lipoic acid blood plasma level is obtained via the present invention is insufficient to obtain a desired therapeutic effect if that level is maintained for only a short period of time e.g. 4 hours or less. However, by using the controlled release formulation of the invention these lower lipoic acid blood plasma levels can be maintained over 8 hours or more, preferably over 12 hours or more and more preferably over 16 hours or more per day. Further, those lipoic acid blood plasma levels over these periods of time are repeatedly obtained over a period of days, preferably weeks or months and more preferably continuously over any period during which the patient would benefit from reduced serum glucose levels—which may be the remainder of the patient's life.

To obtain the desired results a formulation of the invention needs to start with a sufficient amount of lipoic acid such that it is capable of releasing enough lipoic acid per unit of time to obtain the desired lipoic acid serum levels while compensating for lipoic acid which is metabolized. To obtain the desired results the formulation may provide an initial release of lipoic acid quickly and thereafter provide a gradual release which slows over the useful life of the formulation. However, the release may be gradual from the beginning. In either case there is gradual slowing of the rate of release which is compensated for in that some of the previously released lipoic acid remains in the blood serum unmetabolized.

A preferred oral formulation is a tablet which is designed to dissolve gradually over a period of about 8 hours. As the tablet dissolves its reduced size will release smaller and smaller amounts of lipoic acid per unit of time. At the end of the 8 hours another tablet is administered and the process is repeated. To obtain the benefits of the invention the process is continually repeated over a plurality of days, weeks, months or years. By maintaining a minimal lipoic acid blood serum level over time a patient's abnormally high serum glucose levels are reduced and the long term adverse effects of elevated serum glucose levels are avoided.

Combination Formulations

Lipoic acid acts directly on muscle cells to stimulate glucose transport. The effect on serum glucose reduction obtained with lipoic acid may be sufficient for some patients. However, if an insufficient glucose lowering effect results the lipoic acid may be supplemental with one or more orally effective antidiabetic agents selected from the group consisting of sulfonylureas, biguanides and thiazolidiones. Useful sulfonylureas include tolbutamide and glipizide and related compounds such as Amaryl, Pandin and Starlix. These drugs target pancreatic beta cells and stimulate these cells to release insulin. The biguanides include compounds such as metformin, phenformin and buformin. These compounds act on the liver to decrease hepatic glucose output and on the intestine to block glucose uptake into the blood. Thiazolidinediones include compounds such troglitazone, rosaglutazone and pioglitazone. These compounds are believed to sensitize muscle and fat cells to insulin.

Although all or any orally effective antidiabetics can be formulated with or administered along with the formulation of the invention it is preferable to administer metformin (particularly metformin Hydrochloride tablets sold as Glucophage®) with controlled release lipoic acid formulations of the invention. Some particularly preferred formulations include 300 mg lipoic acid and 500 mg of metformin hydrochloride or if a larger dose is needed 600 mg of lipoic acid and 1,000 mg of metformin hydrochloride. Additional enhanced effects may be obtained by taking lipoic acid with vitamin C and/or vitamin E. For example a patient might take 900 mg/day of lipoic acid 1,000 to 3,000 mg/day of vitamin C and 400 to 800 mg/day of vitamin E.

Example 10 provides specific examples of patient's which underwent coadministration of controlled release lipoic acid formulations of the present invention in combination with other treatments conventionally used to lower serum glucose levels. The synergistic effects were obtained, i.e. the combination of lipoic acid controlled release formulations of the invention with other therapeutic agents obtained results which were greater than results which might be expected with the administration of either composition by itself.

Excipient Material

Examples provided here show that formulations of the invention may comprise different amounts and ratios of active ingredient and excipient material. Further, different excipients can be used. Particularly preferred excipients and amounts used are recited in the Examples. However, upon reading the disclosure those skilled in the art will come to understand the general concepts of the invention and will recognize that other excipients, amounts, ratios and combinations might be used to obtain the results first shown here.

The type and amount of excipient material is added to obtain a formulation with two important characteristics. First, the resulting formulation protects the active ingredient from chemical degradation in the patient's gastrointestinal tract. A formulation of pure, unprotected lipoic acid is not part of the scope of the present invention in that pure lipoic acid is degraded to some degree in the gastrointestinal tract. Although the formulation need not protect 100% of the lipoic acid from degradation to come within the scope of the invention it should protect at least 90% or more, preferably 95% or more and more preferably 99% or more of the lipoic acid from degradation. Although multiple doses of an oral formulation could be taken it is preferable to design the dosage such that a single dose is taken at each dosing event—preferably three times a day and more preferably twice a day. The better the active ingredient is protected from degradation the less active ingredient is needed in the original dosage thereby reducing manufacturing costs and increasing profits. The formulation must protect at least as much of the dose as is needed to obtain a pharmacological effect and preferably obtain the desired treatment results, e.g. maintaining a desired lipoic acid serum level needed to obtain a reduced serum glucose level over time. Excipient materials of the formulations disclosed here are particularly useful at protecting the lipoic acid in a high pH environment of the lower gastrointestinal tract of a human.

The second necessary characteristic of the formulation is that it does not release all of the active ingredient at one time but rather releases the active ingredient gradually over time. This is particularly important because (1) lipoic acid has a relatively short half life and (2) a desired level of lipoic acid in blood serum must be maintained over a long period to obtain the desired effect. If all of the lipoic acid is released at once it will all enter the circulatory system at once and be metabolized in the liver thereby causing the lipoic acid serum level to drop below the desired level. When this occurs the effect on reducing glucose levels is suboptimal.

Typical Formulations

A typical formulation of the invention will contain about 50% to 70% by weight of lipoic acid and a particularly preferred formulation will comprise 60% by weight of lipoic acid. Assuming a formulation with 60% by weight of lipoic acid with the remaining 40% being excipient material there are a number of possible components which could be used to make up that 40%. A generalized and specific description of such is provided below:

| (1) | lipoic acid | 60% |
| | organic polymer | 40% |
| | TOTAL | 100% |
| (2) | lipoic acid | 60% |
| | organic polymer | 34.5% |
| | inorganics | 5.5% |
| | TOTAL | 100% |
| (3) | lipoic acid | 60% |

-continued

| | organic polymer | 30%–40% |
| | inorganics | 10% or less |
| | TOTAL | 100% |
| (4) | lipoic acid | 60% |
| | microcrystalline cellulose | 14% |
| | cellulose acetate phthalate aqueous dispersion | 15% |
| | polyvinylpyraolidone | 3% |
| | ethyl acetate | 2.5% |
| | hydrous magnesium silicate (talc) | 1% |
| | carboxy methyl ether | 4% |
| | magnesium stearate | 0.5% |
| | TOTAL | 100% |
| (5) | lipoic acid | 60% |
| | microcrystalline cellulose | 10–30% |
| | cellulose acetate phthalate aqueous dispersion | 5–25% |
| | polyvinylpyraolidone | 1–5% |
| | ethyl acetate | 1–5% |
| | hydrous magnesium silicate (talc) | 0.5–3% |
| | carboxy methyl ether | 1–5% |
| | magnesium stearate | 0.5–1.5% |
| | TOTAL | 100% |
| (6) | lipoic acid | 60% |
| | microcrystalline cellulose, NF (Avicel PH 101) | 14% |
| | Aquacoat CPD-30 (30% solids w/w) | 15% |
| | Plasdone K29/32, USP | 3% |
| | Carbopol 974P, NF | 2.5% |
| | Talc, USP | 1.0% |
| | croscarmellose sodium, NF (Ac, di-Sol) | 4.0% |
| | Magnesium Stearate, NF | 0.5% |
| | TOTAL | 100% |
| (7) | lipoic acid | 60% |
| | microcrystalline cellulose, NF (Avicel PH 101) | 10–30% |
| | Aquacoat CPD-30 (30% solids w/w) | 5–25% |
| | Plasdone K29/32, USP | 1–5% |
| | Carbopol 974P, NF | 1–5% |
| | Talc, USP | 0.5–3% |
| | croscarmellose sodium, NF (Ac, di-Sol) | 1–5% |
| | Magnesium Stearate, NF | 0.5–1.5% |
| | TOTAL | 100% |

Those skilled in the art will recognize that there are endless possibilities in terms of formulations. Even if the formulations are limited to the relatively few compounds shown above the formulation could be changed in limitless ways by adjusting the ratios of the components to each other. The important feature of any formulation of the invention is that the lipoic acid be released gradually over 4 hours or more, preferably 8 hours or more. Some general types of controlled release technology which might be used with the present invention is described below followed by specific preferred formulations.

Controlled Release Technology

Controlled release within the scope of this invention can be taken to mean any one of a number of extended release dosage forms. The following terms may be considered to be substantially equivalent to controlled release, for the purposes of the present invention: continuous release, controlled release, delayed release, depot, gradual release, long-term release, programmed release, prolonged release, proportionate release, protracted release, repository, retard, slow release, spaced release, sustained release, time coat, timed release, delayed action, extended action, layered-time action, long acting, prolonged action, repeated action, slowing acting, sustained action, sustained-action medications, and extended release. Further discussions of these terms may be found in Lesczek Krowczynski, *Extended-Release Dosage Forms,* 1987 (CRC Press, Inc.).

The various controlled release technologies cover a very broad spectrum of drug dosage forms. Controlled release technologies include, but are not limited to physical systems and chemical systems. Physical systems include, but not limited to, reservoir systems with rate-controlling membranes, such as microencapsulation, macroencapsulation, and membrane systems; reservoir systems without rate-controlling membranes, such as hollow fibers, ultra microporous cellulose triacetate, and porous polymeric substrates and foams; monolithic systems, including those systems physically dissolved in non-porous, polymeric, or elastomeric matrices (e.g., non-erodible, erodible, environmental agent ingression, and degradable), and materials physically dispersed in non-porous, polymeric, or elastomeric matrices (e.g., non-erodible, erodible, environmental agent ingression, and degradable); laminated structures, including reservoir layers chemically similar or dissimilar to outer control layers; and other physical methods, such as osmotic pumps, or adsorption onto ion-exchange resins.

Chemical systems include, but are not limited to, chemical erosion of polymer matrices (e.g., heterogeneous, or homogeneous erosion), or biological erosion of a polymer matrix (e.g., heterogeneous, or homogeneous). Additional discussion of categories of systems for controlled release may be found in Agis F. Kydonieus, *Controlled Release Technologies; Methods, Theory and Applications,* 1980 (CRC Press, Inc.).

Controlled release drug delivery systems may also be categorized under their basic technology areas, including, but not limited to, rate-preprogrammed drug delivery systems, activation-modulated drug delivery systems, feedback-regulated drug delivery systems, and site-targeting drug delivery systems.

In rate-preprogrammed drug delivery systems, release of drug molecules from the delivery systems "preprogrammed" at specific rate profiles. This may be accomplished by system design, which controls the molecular diffusion of drug molecules in and/or across the barrier medium within or surrounding the delivery system. Fick's laws of diffusion are often followed.

In activation-modulated drug delivery systems, release of drug molecules from the delivery systems is activated by some physical, chemical or biochemical processes and/or facilitated by the energy supplied externally. The rate of drug release is then controlled by regulating the process applied, or energy input.

In feedback-regulated drug delivery systems, release of drug molecules from the delivery systems may be activated by a triggering event, such as a biochemical substance, in the body. The rate of drug release is then controlled by the concentration of triggering agent detected by a sensor in the feedback regulated mechanism.

In a site-targeting controlled-release drug delivery system, the drug delivery system targets the active molecule to a specific site or target tissue or cell. This may be accomplished, for example, by a conjugate including a site specific targeting moiety that leads the drug delivery system to the vicinity of a target tissue (or cell), a solubilizer that enables the drug delivery system to be transported to and preferentially taken up by a target tissue, and a drug moiety that is covalently bonded to the polymer backbone through a spacer and contains a cleavable group that can be cleaved only by a specific enzyme at the target tissue.

While a preferable mode of controlled release drug delivery will be oral, other modes of delivery of controlled release compositions according to this invention may be used. These include mucosal delivery, nasal delivery, ocular delivery, transdermal delivery, parenteral controlled release delivery, vaginal delivery, rectal delivery, and intrauterine delivery.

There are a number of controlled release drug formulations that are developed preferably for oral administration. These include, but are not limited to, osmotic pressure-controlled gastrointestinal delivery systems; hydrodynamic pressure-controlled gastrointestinal delivery systems; membrane permeation-controlled gastrointestinal delivery systems, which include microporous membrane permeation-controlled gastrointestinal delivery devices; gastric fluid-resistant intestine targeted controlled-release gastrointestinal delivery devices; gel diffusion-controlled gastrointestinal delivery systems; and ion-exchange-controlled gastrointestinal delivery systems, which include cationic and anionic drugs. Additional information regarding controlled release drug delivery systems may be found in Yie W. Chien, *Novel Drug Delivery Systems,* 1992 (Marcel Dekker, Inc.). some of these formulations will now be discussed in more detail.

Enteric coatings may be applied to tablets to prevent the release of drugs in the stomach either to reduce the risk of unpleasant side effects or to maintain the stability of the drug which might otherwise be subject to degradation of expose to the gastric environment. Most polymers that are used for this purpose are polyacids that function by virtue or the fact that their solubility in aqueous medium is pH-dependent, and they require conditions with a pH higher then normally encountered in the stomach.

Enteric coatings may be used to coat a solid or liquid dosage form of the lipoates. Enteric coatings promote the lipoates' remaining physically incorporated in the dosage form for a specified period when exposed to gastric juice. Yet the enteric coatings are designed to disintegrate in intestinal fluid for ready absorption. Delay of the lipoates' absorption is dependent on the rate of transfer through the gastrointestinal tract, and so the rate of gastric emptying is an important factor. Some investigators have reported that a multiple-unit type dosage form, such as granules, may be superior to a single-unit type. Therefore, in a preferable embodiment, the lipoates may be contained in an enterically coated multiple-unit dosage form. In a more preferable embodiment, the lipoate dosage form is prepared by spray-coating granules of an lipoate-enteric coating agent solid dispersion on an inert core material. These granules can result in prolonged absorption of the drug with good bioavailability.

Typical enteric coating agents include, but are not limited to, hydroxypropylmethylcellulose phthalate, methacrylic acid-methacrylic acid ester copolymer, polyvinyl acetate-phthalate and cellulose acetate phthalate. Akihiko Hasegawa, *Application of solid dispersions of Nifedipine with enteric coating agent to prepare a sustained-release dosage form,* Chem. Pharm. Bull. 33: 1615–1619 (1985). Various enteric coating materials may be selected on the basis of testing to achieve an enteric coated dosage form designed ab initio to have a preferable combination of dissolution time, coating thicknesses and diametral crushing strength. S. C. Porter et al., *The Properties of Enteric Tablet Coatings Made From Polyvinyl Acetate-phthalate and Cellulose acetate Phthalate*, J. Pharm. Pharmacol. 22:42p (1970).

On occasion, the performance of an enteric coating may hinge on its permeability. S. C. Porter et al., *The Permeability of Enteric Coatings and the Dissolution Rates of Coated Tablets*, J. Pharm. Pharmacol. 34: 5–8 (1981). With such oral drug delivery systems, the drug release process may be initiated by diffusion of aqueous fluids across the enteric coating. Investigations have suggested osmotic driven/rupturing affects as important release mechanisms from enteric coated dosage forms. Roland Bodmeier et al., *Mechanical Properties of Dry and Wet Cellulosic and Acrylic Films Prepared from Aqueous Colloidal Polymer Dispersions used in the Coating of Solid Dosage Forms*, Pharmaceutical Research, 11: 882–888 (1994).

Another type of useful oral controlled release structure is a solid dispersion. A solid dispersion may be defined as a dispersion of one or more active ingredients in an inert carrier or matrix in the solid state prepared by the melting (fusion), solvent, or melting-solvent method. Akihiko Hasegawa, *Super Saturation Mechanism of Drugs from Solid Dispersions with Enteric Coating Agents*, Chem. Pharm. Bull. 36: 4941–4950 (1998). The solid dispersions may be also called solid-state dispersions. The term "coprecipitates" may also be used to refer to those preparations obtained by the solvent methods.

Solid dispersions may be used to improve the solubilities and/or dissolution rates of poorly water-soluble lipoates. See generally Hiroshi Yuasa, et al., *Application of the Solid Dispersion Method to the Controlled Release Medicine, III, Control of the Release Rate of Slightly Water-Soluble Medicine From Solid Dispersion Granules*, Chem. Pharm. Bull. 41:397–399 (1993). The solid dispersion method was originally used to enhance the dissolution rate of slightly water-soluble medicines by dispersing the medicines into water-soluble carriers such as polyethylene glycol or polyvinylpyrrolidone, Hiroshi Yuasa, et al., *Application of the Solid Dispersion Method to the Controlled Release of Medicine, IV Precise Control of the Release Rate of a Water-Soluble Medicine by Using the Solid Dispersion Method Applying the Difference in the Molecular Weight of a Polymer*, Chem. Pharm. Bull. 41:933–936 (1993).

The selection of the carrier may have an influence on the dissolution characteristics of the dispersed drug because the dissolution rate of a component from a surface may be affected by other components in a multiple component mixture. For example, a water-soluble carrier may result in a fast release of the drug from the matrix, or a poorly soluble or insoluble carrier may lead to a slower release of the drug from the matrix. The solubility of the lipoates may also be increased owing to some interaction with the carriers.

Examples of carriers useful in solid dispersions according to the invention include, but are not limited to, water-soluble polymers such as polyethylene glycol, polyvinylpyrrolidone, or hydroxypropylmethyl-cellulose. Akihiko Hasegawa, *Application of Solid Dispersions of Nifedipine with Enteric Coating Agent to Prepare a Sustained-release Dosage Form*, Chem. Pharm. Bull. 33: 1615–1619 (1985).

Alternate carriers include phosphatidylcholine. Makiko Fujii, et al., *The Properties of Solid Dispersions of Indomethacin, Ketoprofen and Flurbiprofen in Phosphatidylcholine*, Chem. Pharm. Bull. 36:2186–2192 (1988). Phosphatidylcholine is an amphoteric but water-insoluble lipid, which may improve the solubility of otherwise insoluble lipoates in an amorphous state in phosphatidylcholine solid dispersions. See Makiko Fujii, et al., *Dissolution of Bioavailibility of Phenytoin in Solid Dispersion with Phosphatidylcholine*, Chem. Pharm. Bull 36:4908–4913 (1988).

Other carriers include polyoxyethylene hydrogenated castor oil. Katsuhiko Yano, et al., *In-Vitro Stability and In-Vivo Absorption Studies of Colloidal Particles Formed From a Solid Dispersion System*, Chem. Pharm. Bull 44:2309–2313 (1996). Poorly water-soluble lipoates may be included in a solid dispersion system with an enteric polymer such as hydroxypropylmethylcellulose phthalate and carboxymethylethylcellulose, and a non-enteric polymer, hydroxypropylmethylcellulose. See Toshiya Kai, et al., *Oral Absorption Improvement of Poorly Soluble Drug Using Soluble Dispersion Technique*, Chem. Pharm. Bull. 44:568–571 (1996). Another solid dispersion dosage form includes incorporation of the drug of interest with ethyl cellulose and stearic acid in different ratios. Kousuke Nakano, et al., *Oral Sustained-Release Cisplatin Preparations for Rats and Mice*, J. Pharm. Pharmacol. 49:485–490 (1997).

There are various methods commonly known for preparing solid dispersions. These include, but are not limited to the melting method, the solvent method and the melting-solvent method.

In the melting method, the physical mixture of a drug in a water-soluble carrier is heated directly until it melts. The melted mixture is then cooled and solidified rapidly while rigorously stirred. The final solid mass is crushed, pulverized and sieved. Using this method a super saturation of a solute or drug in a system can often be obtained by quenching the melt rapidly from a high temperature. Under such conditions, the solute molecule may be arrested in solvent matrix by the instantaneous solidification process. A disadvantage is that many substances, either drugs or carriers, may decompose or evaporate during the fusion process at high temperatures. However, this evaporation problem may be avoided if the physical mixture is heated in a sealed container. Melting under a vacuum or blanket of an inert gas such as nitrogen may be employed to prevent oxidation of the drug or carrier.

The solvent method has been used in the preparation of solid solutions or mixed crystals of organic or inorganic compounds. Solvent method dispersions may prepared by dissolving a physical mixture of two solid components in a common solvent, followed by evaporation of the solvent. The main advantage of the solvent method is that thermal decomposition of drugs or carriers may be prevented because of the low temperature required for the evaporation of organic solvents. However, some disadvantages associated with this method are the higher cost of preparation, the difficulty in completely removing liquid solvent, the possible adverse effect of its supposedly negligible amount of the solvent on the chemical stability of the drug.

Another method of producing solid dispersions is the melting-solvent method. It is possible to prepare solid dispersions by first dissolving a drug in a suitable liquid solvent and then incorporating the solution directly into a melt of polyethylene glycol, obtainable below 70 degrees, without removing the liquid solvent. The selected solvent or dissolved lipoate may be selected such that the solution is not miscible with the melt of polyethylene glycol. The polymorphic form of the lipoate may then be precipitated in the melt. Such a unique method possesses the advantages of both the melting and solvent methods. Win Loung Chiou, et al., *Pharmaceutical Applications of Solid Dispersion Systems*, J. Pharm. Sci. 60:1281–1301 (1971).

Another controlled release dosage form is a complex between an ion exchange resin and the lipoates. Ion exchange resin-drug complexes have been used to formulate sustained-release products of acidic and basic drugs. In one preferable embodiment, a polymeric film coating is provided to the ion exchange resin-drug complex particles, making drug release from these particles diffusion controlled. See Y. Raghunathan et al., *Sustained-released drug delivery system I: Coded ion-exchange resin systems for phenylpropanolamine and other drugs*, J. Pharm. Sciences 70: 379–384 (1981).

Injectable micro spheres are another controlled release dosage form. Injectable micro spheres may be prepared by non-aqueous phase separation techniques, and spray-drying techniques. Micro spheres may be prepared using polylactic acid or copoly(lactic/glycolic acid). Shigeyuki Takada, *Utilization of an Amorphous Form of a Water-Soluble GPIIb/IIIa Antagonist for Controlled Release From Biodegradable Micro spheres*, Pharm. Res. 14:1146–1150 (1997), and ethyl cellulose, Yoshiyuki Koida, *Studies on Dissolution Mechanism of Drugs from Ethyl Cellulose Microcapsules*, Chem. Pharm. Bull. 35:1538–1545 (1987).

Other controlled release technologies that may be used in the practice of this invention are quite varied. They include SODAS, INDAS, IPDAS, MODAS, EFVAS, PRODAS, and DUREDAS (SODAS, INDAS, IPDAS, MODAS, EFVAS, PRODAS, and DUREDAS may be trademarks of the Elan Corporation). SODAS are multi particulate dosage forms utilizing controlled release beads. INDAS are a family of drug delivery technologies designed to increase the solubility of poorly soluble drugs. IPDAS are multi particulate tablet formation utilizing a combination of high density controlled release beads and an immediate release granulate. MODAS are controlled release single unit dosage forms. Each tablet consists of an inner core surrounded by a semipermeable multiparous membrane that controls the rate of drug release. EFVAS is an effervescent drug absorption system. PRODAS is a family of multi particulate formulations utilizing combinations of immediate release and controlled release mini-tablets. DUREDAS is a bilayer tablet formulation providing dual release rates within the one dosage form. Although these dosage forms are known to one of skill, certain of these dosage forms will now be discussed in more detail.

INDAS was developed specifically to improve the solubility and absorption characteristics of poorly water soluble drugs. Solubility and, in particular, dissolution within the fluids of the gastrointestinal tract is a key factor in determining the overall oral bioavailability of poorly water soluble drug. By enhancing solubility, one can increase the overall bioavailability of a drug with resulting reductions in dosage. INDAS takes the form of a high energy matrix tablet. In a preferred embodiment of the invention, production involves including lipoic acid in an amorphous form together with a combination of energy, excipients, and unique processing procedures.

Once included in the desirable physical form, the resultant high energy complex may be stabilized by an absorption process that utilizes a novel polymer cross-linked technology to prevent recrystallization. The combination of the change in the physical state of the lipoate coupled with the solubilizing characteristics of the excipients employed enhances the solubility of the lipoate. The resulting absorbed amorphous drug complex granulate may be formulated with a gel-forming erodible tablet system to promote substantially smooth and continuous absorption.

IPDAS is a multi-particulate tablet technology that may enhance the gastrointestinal tolerability of potential irritant and ulcerogenic drugs. Intestinal protection is facilitated by the multi-particulate nature of the IPDAS formulation which promotes dispersion of an irritant lipoate throughout the gastrointestinal tract. Controlled release characteristics of the individual beads may avoid high concentration of drug being both released locally and absorbed systemically. The combination of both approaches serves to minimize the potential harm of the lipoates with resultant benefits to patients.

IPDAS is composed of numerous high density controlled release beads. Each bead may be manufactured by a two step process that involves the initial production of a micromatrix with embedded lipoates and the subsequent coating of this micromatrix with polymer solutions that form a rate limiting semipermeable membrane in vivo. Once an IPDAS tablet is ingested, it may disintegrate and liberate the beads in the stomach. These beads may subsequently pass into the duodenum and along the gastrointestinal tract, preferably in a controlled and gradual manner, independent of the feeding state. Lipoate release occurs by diffusion process through the micromatrix and subsequently through the pores in the rate controlling semipermeable membrane. The release rate from the IPDAS tablet may be customized to deliver a drug-specific absorption profile associated with optimized clinical benefit. Should a fast onset of activity be necessary, immediate release granulate may be included in the tablet. The tablet may be broken prior to administration, without substantially compromising drug release, if a reduced dose is required for individual titration.

MODAS is a drug delivery system that may be used to control the absorption of water soluble lipoates. Physically MODAS is a non-disintegrating table formulation that manipulates drug release by a process of rate limiting diffusion by a semipermeable membrane formed in vivo. The diffusion process essentially dictates the rate of presentation of drug to the gastrointestinal fluids, such that the uptake into the body is controlled. Because of the minimal use of excipients, MODAS can readily accommodate small dosage size forms. Each MODAS tablet begins as a core containing active drug plus excipients. This core is coated with a solution of insoluble polymers and soluble excipients. Once the tablet is ingested, the fluid of the gastrointestinal tract may dissolve the soluble excipients in the outer coating leaving substantially the insoluble polymer. What results is a network of tiny, narrow channels connecting fluid from the gastrointestinal tract to the inner drug core of water soluble drug. This fluid passes through these channels, into the core, dissolving the drug, and the resultant solution of drug may diffuse out in a controlled manner. This may permit both controlled dissolution and absorption. An advantage of this system is that the drug releasing pores of the tablet are distributed over substantially the entire surface of the tablet. This facilitates uniform drug absorption reduces aggressive unidirectional drug delivery. MODAS represents a very flexible dosage form in that both the inner core and the outer semipermeable membrane may be altered to suit the individual delivery requirements of a drug. In particular, the addition of excipients to the inner core may help to produce a microenvironment within the tablet that facilitates more predictable release and absorption rates. The addition of an immediate release outer coating may allow for development of combination products.

Additionally, PRODAS may be used to deliver lipoates according to the invention. PRODAS is a multi particulate drug delivery technology based on the production of controlled release mini tablets in the size range of 1.5 to 4 mm in diameter. The PRODAS technology is a hybrid of multi particulate and hydrophilic matrix tablet approaches, and may incorporate, in one dosage form, the benefits of both these drug delivery systems.

In its most basic form, PRODAS involves the direct compression of an immediate release granulate to produce individual mini tablets that contain lipoates. These mini tablets are subsequently incorporated into hard gels and capsules that represent the final dosage form. A more beneficial use of this technology is in the production of controlled release formulations. In this case, the incorporation of various polymer combinations within the granulate may delay the release rate of drugs from each of the individual mini tablets. These mini tablets may subsequently be coated with controlled release polymer solutions to provide additional delayed release properties. The additional coating may be necessary in the case of highly water soluble drugs or drugs that are perhaps gastroirritants where release can be delayed until the formulation reaches more distal regions of the gastrointestinal tract. One value of PRODAS technology lies in the inherent flexibility to formulation whereby combinations of mini tablets, each with different release rates, are incorporated into one dosage form. As well as potentially permitting controlled absorption over a specific period, this also may permit targeted delivery of drug to specific sites of absorption throughout the gastrointestinal tract. Combination products also may be possible using mini tablets formulated with different active ingredients.

DUREDAS is a bilayer tableting technology that may be used in the practice of the invention. DUREDAS was developed to provide for two different release rates, or dual release of a drug from one dosage form. The term bilayer refers to two separate direct compression events that take place during the tableting process. In a preferable embodiment, an immediate release granulate is first compressed, being followed by the addition of a controlled release element which is then compressed onto this initial tablet. This may give rise to the characteristic bilayer seen in the final dosage form.

The controlled release properties may be provided by a combination of hydrophilic polymers. In certain cases, a rapid release of the lipoic acid may be desirable in order to facilitate a fast onset of therapeutic affect. Hence one layer of the tablet may be formulated as an immediate release granulate. By contrast, the second layer of the tablet may release the drug in a controlled manner, preferably through the use of hydrophilic polymers. This controlled release may result from a combination of diffusion and erosion through the hydrophilic polymer matrix.

A further extension of DUREDAS technology is the production of controlled release combination dosage forms. In this instance, two different lipoic acid compounds may be incorporated into the bilayer tablet and the release of drug from each layer controlled to maximize therapeutic affect of the combination.

Furthermore, compositions and lipoates according to the invention may be administered or coadministered with conventional pharmaceutical excipients and additives. These include, but are not limited to, gelatin, natural sugars such as raw sugar or lactose, lecithin, mucilage, plant gums, pectins or pectin derivatives, algal polysaccharides, glucomannan, agar and lignin, guar gum, locust bean gum, acacia gum, xanthan gum, carrageenan gum, karaya gum, tragacanth gum, ghatti gum, starches (for example corn starch or amylose), dextran, polyvinyl pyrrolidone, polyvinyl acetate, gum arabic, alginic acid, tylose, talcum, lycopodium, silica gel (for example colloidal), cellulose and cellulose derivatives (for example cellulose ethers, cellulose ethers in which the cellulose hydroxy groups are partially etherified with lower saturated aliphatic alcohols and/or lower saturated, aliphatic oxyalcohols, for example methyl oxypropyl cellulose, methyl cellulose, hydroxypropyl methyl cellulose, hydroxypropyl methyl cellulose phthalate, cross-linked sodium carboxymethylcellulose, cross-linked hydroxypropylcellulose, high-molecular weight hydroxymethylpropycellulose, carboxymethyl-cellulose, low-molecular weight hydroxypropylmethylcellulose medium-viscosity hydroxypropylmethylcellulose hydroxyethylcellulose, hydroxypropylcellulose, hydroxypropylmethylcellulose, sodium carboxymethylcelulose, alkylcelluloses, ethyl cellulose, cellulose acetate, cellulose propionate (lower, medium or higher molecular weight), cellulose acetate propionate, cellulose acetate butyrate, cellulose triacetate, methyl cellulose, hydroxypropyl cellulose, or hydroxypropylmethyl cellulose), fatty acids as well as magnesium, calcium or aluminum salts of fatty acids with 12 to 22 carbon atoms, in particular saturated (for example stearates such as magnesium stearate), polycarboxylic acids, emulsifiers, oils and fats, in particular vegetable (for example, peanut oil, castor oil, olive oil, sesame oil, cottonseed oil, corn oil, wheat germ oil, sunflower seed oil, cod liver oil, in each case also optionally hydrated); glycerol esters and polyglycerol esters of saturated fatty acids $C_{12}H_{24}O_2$ to $C_{18}J_{36}O_2$ and their mixtures, it being possible for the glycerol hydroxy groups to be totally or also only partly esterified (for example mono-, di- and triglycerides); pharmaceutically acceptable mono- or multivalent alcohols and polyglycols such as polyethylene glycol and derivatives thereof, esters of aliphatic saturated or unsaturated fatty acids (2 to 22 carbon atoms, in particular 10–18 carbon atoms) with monovalent aliphatic alcohols (1 to 20 carbon atoms) or multivalent alcohols such as glycols, glycerol, diethylene glycol, pentacrythritol, sorbitol, mannitol and the like, which may optionally also be etherified, esters of citric acid with primary alcohols, acetic acid, urea, benzyl benzoate, dioxolanes, glyceroformals, tetrahydrofurfuryl alcohol, polyglycol ethers with $C_1$–$C_{12}$-alcohols, dimethylacetamide, lactamides, lactates, ethylcarbonates, silicones (in particular medium-viscous polydimethyl siloxanes), calcium carbonate, sodium carbonate, calcium phosphate, sodium phosphate, magnesium carbonate and the like.

Other substances that may be used include: cross-linked polyvinyl pyrrolidone, carboxymethylamide, potassium methacrylatedivinylbenzene copolymer, high-molecular weight polyvinylacohols, low-molecular weight polyvinylalcohols, medium-viscosity polyvinylalcohols, polyoxyethyleneglycols, non-cross linked polyvinylpyrrolidone, polyethylene glycol, sodium alginate, galactomannone, carboxypolymethylene, sodium carboxymethyl starch, sodium carboxymethyl cellulose or microcrystalline cellulose; polymerizates as well as copolymerizates of acrylic acid and/or methacrylic acid and/or their esters, such as, but not limited to poly(methyl methacrylate), poly(ethyl methacrylate), poly(butyl methacylate), poly (isobutyl methacrylate), poly(hexyl methacrylate), poly (isodecyl methacrylate), poly(lauryl methacrylate), poly (phenyl methacrylate), poly(methyl acrylate), poly (isopropyl acrylate), poly(isobutyl acrylate), or poly (octadecyl acrylate); copolymerizates of acrylic and methacrylic acid esters with a lower ammonium group content (for example Eudragit® RS, available from Rohm, Somerset, N.J.), copolymerizates of acrylic and methacrylic acid esters and trimethyl ammonium methacrylate (for example Eudragit® RL, available from Rohm, Somerset, N.J.); polyvinyl acetate; fats, oils, waxes, fatty alcohols; hydroxypropyl methyl cellulose phthalate or acetate succinate; cellulose acetate phthalate, starch acetate phthalate as well as polyvinyl acetate phthalate, carboxy methyl cellulose; methyl cellulose phthalate, methyl cellulose succinate, -phthalate succinate as well as methyl cellulose phthalic acid half ester; zein; ethyl cellulose as well as ethyl cellulose succinate; shellac, gluten; ethylcarboxyethyl cellulose; ethylacrylate-maleic acid anhydride copolymer; maleic acid anhydride-vinyl methyl ether copolymer; styrol-maleic acid copolymerizate; 2-ethyl-hexyl-acrylate maleic acid anhydride; crotonic acid-vinyl acetate copolymer; glutaminic acid/glutamic acid ester copolymer; carboxymethylethylcellulose glycerol monooctanoate; cellulose acetate succinate; polyarginine; poly(ethylene), poly(ethylene) low density, poly(ethylene) high density, poly(propylene), poly(ethylene oxide), poly(ethylene terephthalate), poly(vinyl isobutyl ether), poly(vinyl chloride) or polyurethane. Mixtures of any of the substances or materials listed herein may also be used in the practice of the invention.

Plasticizing agents that may be considered as coating substances useful are: Citric and tartaric acid esters (acetyltriethyl citrate, acetyl tributyl-, tributyl-, triethyl-citrate); glycerol and glycerol esters (glycerol diacetate, -triacetate, acetylated monoglycerides, castor oil); phthalic acid esters (dibutyl-, diamyl-, diethyl-, dimethyl-, dipropyl-phthalate), di-(2-methoxy- or 2-ethoxyethyl)-phthalate, ethylphthalyl glycolate, butylphthalylethyl glycolate and butylglycolate; alcohols (propylene glycol, polyethylene glycol of various chain lengths), adipates (diethyladipate, di-(2-methoxy- or 2-ethoxyethyl)-adipate; benzophenone; diethyl- and diburylsebacate, dibutylsuccinate, dibutyltartrate; diethylene glycol dipropionate; ethyleneglycol diacetate, -dibutyrate, -dipropionate; tributyl phosphate, tributyrin; polyethylene glycol sorbitan monooleate (polysorbates such as Polysorbar 50); sorbitan monooleate.

The lipoates according to the invention may be orally administered or coadministered in a liquid dosage form. For the preparation of solutions or suspensions it is, for example, possible to use water or physiologically acceptable organic solvents, such as alcohols (ethanol, propanol, isopropanol, 1,2-propylene glycol, polyglycols and their derivatives, fatty alcohols, partial esters of glycerol), oils (for example peanut oil, olive oil, sesame oil, almond oil, sunflower oil, soya bean oil, castor oil, bovine hoof oil), paraffins, dimethyl sulphoxide, triglycerides and the like.

In the case of drinkable solutions the following substances may be used as stabilizers or solubilizers: lower aliphatic mono- and multivalent alcohols with 2–4 carbon atoms, such as ethanol, n-propanol, glycerol, polyethylene glycols with molecular weights between 200–600 (for example 1 to 40% aqueous solution), diethylene glycol monoethyl ether, 1,2-propylene glycol, organic amides, for example amides of aliphatic C1–C6-carboxylic acids with ammonia or primary, secondary or tertiary C1–C4-amines or C1–C4-hydroxy amines such as urea, urethane, acetamide, N-methyl acetamide, N,N-diethyl acetamide, N,N-dimethyl acetamide, lower aliphatic amines and diamines with 2–6 carbon atoms, such as ethylene diamine, hydroxyethyl theophylline, tromethamine (for example as 0.1 to 20% aqueous solution), aliphatic amino acids.

In preparing the inventive compositions, it is possible to use known and conventional solubilizers or emulsifiers. Solubilizers and emulsifiers that may for example be used are: polyvinyl pyrrolidone, sorbitan fatty acid esters such as sorbitan trioleate, phosphatides such as lecithin, acacia, tragacanth, polyoxyethylated sorbitan monooleate and other ethoxylated fatty acid esters of sorbitan, polyoxyethylated fats, polyoxyethylated oleotriglycerides, linolizated oleotriglycerides, polyethylene oxide condensation products of fatty alcohols, alkylphenols or fatty acids or also 1-methyl-3-(2-hydroxyethyl)imidazolidone-(2). In this context, polyoxyethylated means that the substances in question contain polyoxyethylene chains, the degree of polymerization of which generally lies between 2 and 40 and in particular between 10 and 20.

Polyoxyethylated substances of this kind may for example be obtained by reaction of hydroxyl group-containing compounds (for example mono- or diglycerides or unsaturated compounds such as those containing oleic acid radicals) with ethylene oxide (for example 40 Mol ethylene oxide per 1 Mol glyceride).

Examples of oleotriglycerides are olive oil, peanut oil, castor oil, sesame oil, cottonseed oil, corn oil. See also Dr. H. P. Fiedler "Lexikon der Hillsstoffe für Pharmazie, Kostnetik und angrenzende Gebiete" 1971, pages 191–195.

It is also possible to add preservatives, stabilizers, buffer substances, flavor correcting agents, sweeteners, colorants, antioxidants and complex formers and the like. Complex formers which may be for example be considered are: chelate formers such as ethylene diamine retrascetic acid, nitrilotriacetic acid, diethylene triamine pentacetic acid and their salts.

It may optionally be necessary to stabilize lipoates according to the invention with physiologically acceptable bases or buffers to a pH range of ea. 6 to 9. Preference may be given to as neutral or weakly basic a pH value as possible (up to pH 8).

In some dosage forms, it may be useful to include antioxidants or preservatives. Antioxidants that may for example be used are sodium sulphite, sodium hydrogen sulphite, sodium metabisulphite, ascorbic acid, ascorbylpalmitate, -myristate, -stearate, gallic acid, gallic acid alkyl ester, butylhydroxyamisol, nordihydroguaiaretic acid, tocopherols as well as synergists (substances which bind heavy metals through complex formation, for example lecithin, ascorbic acid, phosphoric acid ethylene diamine tetracetic acid, citrates, tartrates). Addition of synergists substantially increases the antioxygenic effect of the antioxidants.

Preservatives that may for example be considered are sorbic acid, p-hydroxybenzoic acid esters (for example lower alkyl esters), benzoic acid, sodium benzoate, trichloroisobutyl alcohol, phenol, cresol, benzethonium chloride, chlorhexidine and formalin derivatives.

Furthermore, controlled release lipoates according to the invention may be administered separately, or may coadministered with other inventive controlled release lipoates or other therapeutic agents. Coadministration in the context of this invention is defined to mean the administration of more than one therapeutic in the course of a coordinated treatment to achieve an improved clinical outcome. Such coadministration may also be coextensive, that is, occurring during overlapping periods of time.

The α-lipoic acid of the invention can be incorporated into any one of the aforementioned controlled released dosage forms, or other conventional dosage forms. The amount of α-lipoic acid contained in each dose can be adjusted, to meet the needs of the individual patient, and the indication. One of skill in the art will readily recognize how to adjust the level of α-lipoic acid and the release rates in a controlled release formulation, in order to optimize delivery of α-lipoic acid and its bioavailability. In a preferable embodiment, the amount of α-lipoic acid in a dose ranges from about 25 mg. to about 1000 mg. In a more preferable embodiment, the amount of α-lipoic acid in a dose ranges from about 100 mg. to about 500 mg. In a still more preferable embodiment, the amount of α-lipoic acid in a dose is about 300 mg.

Indications treatable using the invention include diseases impacted by antioxidants; diseases involving carbohydrate metabolism and blood glucose disposal, including various forms of diabetes; protection of the eyes and skin; immunomodulation; protection of the liver and kidneys; cardiovascular production; liver diseases; HIV infection; and neurodegenerative diseases. Additional indications treatable using this invention include, but are not limited to, inflammatory, degenerative articular and extra-articular rheumatic disorders, non-rheumatic states of inflammation and swelling, Arthrosis deformans, chondropathies, periarthritis, neurodermitis and psoriasis, gastritis, Ulcus ventriculi, ileitis, duodenitis, jejunitis, colitis, polyneuropathy of diabetogenic, alcoholic, hepatic and uraemic origin, degeneration of the liver parenchyma, hepatitis, fatty liver and fatty cirrhosis as well as chronic liver disorders, bronchial asthma, sarcoidosis, and ARDS (acute respiratory distress syndrome).

The compound α-lipoic acid has been disclosed as being useful in the treatment of the above indications. The controlled release formulations of the present invention also have utility in the treatment of these indications.

Dosages of the controlled release formulations of the present invention for treatment of these indications may be optimized by one of skill, using conventional dosing trials.

Additionally, controlled release lipoic acid formulations according to this invention may have improved effect versus immediate release acid. These effects include improved bioavailability (AUC); prolonged mean residence time (MRT) in blood; decreased effects of acid lability; and changing the ratio of lipoic acid metabolites, such as dihydrolipoic acid, 3-ketolipoic acid, 3-methoxylipoic acid, 2-unsaturated lipoic acid, bisnorlipoic acid, tetranorlipoic acid, and β-hydroxybisnorlipoic acid, with respect to one another. Additional effects noted include appetite suppression, increased IGF 1 levels, increased testosterone, increased anti-oxidant status, mitochondrial DNA preservation, improved PDH in congestive heart disease, weight loss in Type II diabetics, increased lean body mass, anti-depressant effects, improved energy in diabetic patients, improvements in the quality of sleep, increased serotonin levels, decreased susceptibility to common colds, and improved skin appearance.

Therapeutic Indications

The controlled release lipoic acid formulations of the present invention can be used to obtain a wide range of desirable effects. Particularly the formulations of the invention are useful in treating essentially any disease state or symptom which is treatable by long term administration of antioxidants. Further, the invention can be used in the treatment of diseases which involve carbohydrate metabolism and blood glucose disposal which includes various forms of diabetes. Further, the invention is useful in the treatment of various adverse effects on the eyes and skin when the adverse effect are due to high levels of free radicals which can be dissipated by the presence of antioxidants or high levels of serum glucose which can be reduced by stimulating basal glucose transport. Maintaining substantially constant levels of lipoic acid provides a long term antioxidant effect which assists in immunomodulation and can result in improved liver and kidney function. Because of the long term antioxidant effect in the circulatory system the present invention has a variety of beneficial effects on the cardiovascular system and in the alleviation of certain liver diseases as well as neurodegenerative diseases. A patient infected with HIV can benefit from the enhanced effect obtained on the immune system.

The data provided here do not show specific treatments of many of the diseases or symptoms mentioned above. However, the invention is believed to be responsible for obtaining a wide range of beneficial effects particularly when the controlled release formulation is administered to patient's over long periods of time, i.e. weeks, months and years. By maintaining substantially constant levels of lipoic acid in the blood over very long periods of time a range of desirable physiological results are obtained. Stated differently by continually maintaining the constant serum levels of the powerful antioxidant and keeping a patient's blood glucose level within a more desirable range the adverse effects obtained from free radicals and high fluctuating glucose levels are avoided.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

In a first step, racemic α-lipoic acid is screened to a particle size range of 150 to 450 microns. The racemic α-lipoic acid is then added to a Glatt (Ramsey, N.J.) fluid bed granulator. The racemic α-lipoic acid particles become the cores for a coated particle. The cores are coated with a 30% w/w aqueous dispersion of EUDRAGIT® (NE30 D, methacrylic acid ester) and talc. This yields coated particles with a dried coating weight equal to about 10% of the total weight of the coated particle. The inlet air temperature is kept at a temperature of 25 deg C. After drying, the coated particles are screened using a 40 mesh screen.

The resulting, free-flowing particles are then blended and directly compressed using a tableting press according to the following formula:

Racemic α-lipoic acid, coated particles 81%
METHOCEL® K100 10% (methylcellulose)
Microcrystalline cellulose 5%
Stearic Acid 3%
Micronized silica 0.5%
Magnesium Stearate 0.5%

The resulting tablet is a sustained release formulation.

Example 2

In a first step, R-(+)-α-lipoic acid is screened to a particle size range of 150 to 450 microns. The R-(+)-α-lipoic acid is then added to a Glatt (Ramsey, N.J.) fluid bed granulator. The R-(+)-α-lipoic acid particles become the cores for a coated particle. The cores are coated with a 30% w/w aqueous dispersion of EUDRAGIT® (NE30 D, methacrylic acid ester) and talc. This yields coated particles with a dried coating weight equal to about 10% of the total weight of the coated particle. The inlet air temperature is kept at a temperature of 25 deg C. After drying, the coated particles are screened using a 40 mesh screen.

The resulting, free-flowing particles are then blended and directly compressed using a tableting press according to the following formula:

R-(+)-α-lipoic acid, coated particles 81%
METHOCEL® K100 10% (methylcellulose)
Microcrystalline cellulose 5%
Stearic Acid 3%
Micronized silica 0.5%
Magnesium Stearate 0.5%

The resulting tablet is a sustained release formulation.

Example 3

In a first step, R-(+)-α-lipoic acid is screened to a particle size range of 150 to 450 microns. The R-(+)-α-lipoic acid is then added to a Glatt (Ramsey, N.J.) fluid bed granulator. The R-(+)-α-lipoic acid particles become the cores for a coated particle. EUDRAGIT® (L/S 100, methacrylic acid ester) is dissolved in isopropyl alcohol to form a 15% w/w solution. Triethyl citrate, talc, and water are additionally added to the solution. Total solids content of the resulting mixture is 9.6% w/w. This yields coated particles with a dried coating weight equal to about 10% of the total weight of the coated particle. The inlet air temperature is kept at a temperature of 25 deg C. After drying, the coated particles are screened using a 40 mesh screen.

The resulting, free-flowing particles are then blended and directly compressed using a tableting press according to the following formula:

R-(+)-α-lipoic acid, coated particles 86%
METHOCEL® K100 5% (methylcellulose)
Microcrystalline cellulose 5%
Stearic Acid 3%
Micronized silica 0.5%
Magnesium Stearate 0.5%

The resulting tablet is protected from the harsh acid environment of the stomach, and is delivered to the small intestine where it is gradually released.

Example 4

In a first step, racemic α-lipoic acid is screened to a particle size range of 150 to 450 microns. The racemic α-lipoic acid is then added to a Glatt (Ramsey, N.J.) fluid bed granulator. The racemic α-lipoic acid particles become the cores for a coated particle. EUDRAGIT® (L/S 100, methacrylic acid ester) is dissolved in isopropyl alcohol to form a 15% w/w solution. Triethyl citrate, talc, and water are additionally added to the solution. Total solids content of the resulting mixture is 9.6% w/w. This yields coated particles with a dried coating weight equal to about 10% of the total weight of the coated particle. The inlet air temperature is kept at a temperature of 25 deg C. After drying, the coated particles are screened using a 40 mesh screen.

The resulting, free-flowing particles are then blended and directly compressed using a tableting press according to the following formula:

Racemic α-lipoic acid, coated particles 86%
METHOCEL® K100 5% (methylcellulose)
Microcrystalline cellulose 5%
Stearic Acid 3%
Micronized silica 0.5%
Magnesium Stearate 0.5%

The resulting tablet is protected from the harsh acid environment of the stomach, and is delivered to the small intestine where it is gradually released.

Example 5

A preblend of 98% w/w CARBOPOL® 934 (B. F. Goodrich Chemical, lightly cross-inked acrylic acid allyl sucrose copolymer) and 2% w/w micronized silica is prepared. To this mixture, racemic α-lipoic acid, METHOCEL® K100, stearic acid, and lactose are added according to the following formula:

Racemic α-lipoic acid preblend 70%
CARBOPOLS® 934/silica preblend 10%
METHOCEL®K100 10%
stearic acid 5%
lactose 5%

The resulting mixture is tableted using a direct compression tableting press to form a bioadhesive formulation.

Example 6

A preblend of 98% w/w R-(+)-α-lipoic acid and 2% w/w CAB-O-SIL® micronized silica is formed. To this mixture is added guar gum (AQUALON® G-3), polyvinylpyrrolidone (PVP), calcium carbonate, stearic acid, lactose, and magnesium stearate in the following amounts:

R-(+)-α-lipoic acid/CAB-O-SIL® blend 49.5%
guar gum (AQUALON® G-3) 30%
polyvinylpyrrolidone (PVP) 5%
calcium carbonate 5%
stearic acid 5%
lactose 5%
magnesium stearate 0.5%

The resulting mixture is tableted using a direct compression tableting press to form a stained release caplet formulation.

Example 7

| Item No. | Item Description | Percent | Theoretical Quantity | Unit of Measure |
|---|---|---|---|---|
| 1. | α-Lipoic Acid | 60 | 4800.0 | g |
| 2. | Microcrystalline Cellulose, NF (Avicel PH 101) | 18 | 1440.0 | g |
| 3. | Aquacoat CPD (30% w/w) | 15* | 4000.0* | g |
| 4. | Povidone K29/32, USP | 3 | 240.0 | g |
| 5. | Carbopol 974P | 2.5 | 200.0 | g |
| 6. | Talc, USP | 1 | 80.0 | g |
| 7. | Magnesium Stearate, NF | 0.5 | 40.0 | g |

-continued

| Item No. | Item Description | Percent | Theoretical Quantity | Unit of Measure |
|---|---|---|---|---|
| 8. | Purified Water, USP | | — | g |
| N/A | TOTAL | 100 | 8000.0 | g |

*Quantity indicates amount of dispersion to be used in granulating. Actual Solids Content-1200 g - 15% is based on solids content Before formulating a check should be made of the room and equipment in order to verify that the cleaning procedure has been performed and approved. Weigh and charge α-Lipoic Acid (Item 1) and Avicel PH 101, (Item 2) in a Hobart Mixer and mix for two (2) minutes with the mixer speed set at 1 or 2. Granulate the Step 2 material by slowly adding Aquacoat CPD (Item 3) until granules are formed. Add additional Purified Water, USP (Item 8) if required, and mix until the granules are formed. Mixer Speed Setting remains at 1–2. Spread the granulation evenly from Step 3 on paper-lined trays and load them into the oven. Dry at 40° C.±5° C. for two (2) hours. Check LOD and record moisture content. If LOD is more than 2%, continue drying until LOD is below 2%. Pass the dried material from Step 5 through a size 14 mesh screen, hand held or using a Quadro Comil. Charge the Step 6 granulation into a V-blender. Charge the Step 7 blend in blender with Povidone K29/32, USP (Item 4) and Carbopol 974P (Item 5) and mix for five (5) minutes. Charge the V-blender with Talc (Item 6) and Magnesium Stearate, NF (Item 7) and blend for three (3) minutes. Empty the blend from the V-blender into a properly labeled tared PE-lined container and record the weights in Step 11. Theoretical weight of blend: 8000.0 g. Lower Limit 95% and Upper Limit 102%. Any discrepancy from these established limits must be reported to Production and Quality Assurance. Any discrepancy must be appropriately investigated and documented. Hold the blend in the in-process Q.C. Hold area for further processing. Using the amounts shown above will result in sufficient formulations to produce above 16,000 300 mg tablets.

Example 8

A controlled release oral dosage form of racemic α-lipoic acid was administered to a group of volunteers. Each dose consisted of a tablet containing 300 mg of racemic α-lipoic acid, compounded with calcium phosphate, starch, cellulose ethers, polycarboxylic acid, and magnesium stearate. The 300 mg tablets were produced using components and methods of the type described in Example 7. Two 300 mg tablets were administered in the morning before eating followed by one tablet within 6 to 8 hours.

The results obtained on human volunteers were as follows:

| Patient No. | Sex (M/F) | Age | Average Glucose Levels | |
|---|---|---|---|---|
| | | | Before | After |
| 1 | M | 47 | 240 | 150 |
| 2 | F | 46 | 225 | 120 |
| 3 | M | 45 | 155 | 130 |
| 4 | M | 67 | 155 | 95 |
| 5 | F | 47 | 175 | 195 |
| 6 | M | 82 | 138 | 129 |
| 7 | M | 48 | 174 | 119 |
| 8 | M | 71 | 150 | 90 |

As can be seen from Table 1, the average glucose level before treatment with the controlled release lipoic acid was 176.5 mg/dl. After treatment with the controlled release lipoic acid, the average glucose level was 128.5 mg/dl, a average decrease of 48 mg/dl.

Example 9

A controlled release oral dosage form of racemic α-lipoic acid was administered to a group of volunteers. Each dose consisted of a tablet containing 300 mg of racemic α-lipoic acid, compounded with calcium phosphate, starch, cellulose ethers, polycarboxylic acid, and magnesium stearate. The 300 mg tablets were produced using components and methods of the type described in Example 7. Two 300 mg tablets were administered in the morning before eating followed by one tablet within 6 to 8 hours.

The results were as follows:

| Patient No. | Sex (M/F) | Age | Average Glucose Levels | |
|---|---|---|---|---|
| | | | Before | After |
| 1 | M | 62 | 400 | 140 |
| 2 | F | 65 | 300 | 149 |
| 3 | F | 51 | 325 | 185 |

As can be seen from Table 2, the average glucose level before treatment with the controlled release lipoic acid was 342 mg/dl. After treatment with the controlled release lipoic acid, the average glucose level was 158 mg/dl, a average decrease of 184 mg/dl.

Example 10

Fourteen human volunteers described below were administered controlled release lipoic acid formulations of the present invention. The formulations were prepared in a manner such as that described in Example 7 above. Each patient was dosed with two 300 mg tablets in the morning before eating and one 300 mg tablet approximately six hours thereafter. In some instances some patients were dosed with additional medications as indicated. These results demonstrate the improved results with the lipoic acid controlled release formulations of the invention alone or in combination with other pharmaceutically active compositions.

New CR ALA Tablet Study
Nov-30-98

| Patient # | Type | Description | Age | Average Glucose Levels | | Percent | Comments |
| | | | | Before | After | Change | Change | |
| --- | --- | --- | --- | --- | --- | --- | --- | --- |
| 1 | Type 2 | Glucophage 850 mg 3× | 51 | 220 | 110 | −110 | −50% | |
| 2 | type 2 | Insulin/Glucophage | 70 | 168 | 112 | −56 | −33% | |
| 3 | Type 2 | Insulin/Oral Meds | 54 | 175 | 120 | −55 | −31% | Cut meds in half and 9 to 7 AlC |
| 4 | Type 2 | Glucophage 500 mg 2× Day | 65 | 135 | 114 | −21 | −16% | |
| 6 | type 2 | Diet & Exercise | 46 | 189 | 131 | −58 | −31% | Dr. did not have to put on drugs and drop AlC from 8.3 to 6.2 |
| 7 | Type 2 | Glucophage XL | 67 | 135 | 90 | −45 | −33% | |
| 8 | Type 2 | Insulin/Glucophage | 46 | 300 | 200 | −100 | −33% | |
| 10 | Type 2 | Insulin/Oral Meds | 72 | 185 | 135 | −50 | −27% | |
| 11 | Type 2 | Insulin | 72 | 135 | 87 | −48 | −36% | |
| 12 | Type 2 | Glucophage/Glucotrol | 79 | 225 | 140 | −85 | −38% | |
| 13 | Type 2 | Diet & Exercise | 59 | 145 | 111 | −35 | −24% | |
| 14 | Type 2 | "Insulin, 15 unix 2×" | 51 | 325 | 191 | −134 | −41% | |
| | | AVERAGE = | | 186 | 128 | −57 | −29% | |
| 5 | Normal | Severe polyneuropathy | #N/A | #N/A | #N/A | #N/A | #N/A | Eliminated all neuropath |

The instant invention is shown and described herein in what is considered to be the most practical, and preferred embodiments. It is recognized, however, that departures may be made therefrom, which are within the scope of the invention, and that obvious modifications will occur to one skilled in the art upon reading this disclosure.

What is claimed is:

1. A method of reducing a patient's serum glucose level, comprising:
    administering to the patient a therapeutically effective amount of controlled release lipoic acid,
    wherein the lipoic acid is delivered to the patient's circulatory system at a continual rate over a period of four hours or more;
    wherein the lipoic acid is administered orally;
    wherein the lipoic acid is a racemic mixture administered in an amount in a range of from about 100 mg to about 1,000 mg; and
    wherein the lipoic acid composes a mixture of R-(+)-α-lipoic acid and S-(−)-α-lipoic acid, and ratio of R-(+)-α-lipoic acid to S-(−)-α-lipoic acid ranges from about 90:10 to about 10:90, respectively based on weight.

2. The method of claim 1, wherein the lipoic acid is delivery to the patient's circulatory system so as to maintain a blood serum level of the lipoic acid within a range of from about 25 to about 75 ng/ml of plasma over a period of four hours or more.

3. The method of claim 2, wherein administering is repeated over seven days or more so that the blood plasma level of lipoic acid is maintained over a period of 6 hours or more per day over a period of seven days or more.

4. The method of claim 3, wherein administering is repeated over thirty days or more so that the blood plasma level of lipoic acid is maintained over a period of 12 hours or more per day over a period of thirty days or more.

5. A controlled release oral dosage formulation, comprising:
    a therapeutically effective amount of lipoic acid; and a controlled release
    excipient formulation which releases the lipoic acid in a manner such that the lipoic acid is maintained in the patient's circulatory system at a substantially constant therapeutic level for a period of about four hours or more.

6. The formulation of claim 5, wherein the lipoic acid is released from a physical system comprising reservoir systems with rate-controlling membranes; reservoir systems without rate-controlling membranes; monolithic systems; materials physically dispersed in non-porous, polymeric, or elastomeric matrices; laminated structures; osmotic pumps; or adsorption onto ion-exchange resins.

7. The formulation of claim 5, wherein the lipoic acid is released from a chemical system comprising polymer matrices that are erodible chemically or biologically.

8. The formulation of claim 5, wherein the lipoic acid is released from a controlled release pharmaceutical composition comprising a rate-preprogrammed drug delivery system, an activation-modulated drug delivery system, a feedback-regulated drug delivery system, or a site-targeting drug delivery system.

9. The formulation of claim 5, wherein the lipoic acid is released from a controlled release pharmaceutical composition comprising an enteric coating.

10. The formulation of claim 9, wherein the lipoic acid is released from an enteric coating comprising hydroxypropylmethylcellulose phthalate, methacryclic acid-methacrylic acid ester copolymer, polyvinyl acetate-phthalate and cellulose acetate phthalate.

11. The formulation of claim 5, wherein the lipoic acid is released from a controlled release pharmaceutical composition comprising a solid dispersion.

12. The formulation of claim 11, wherein the lipoic acid is released from a solid dispersion comprising a water soluble or a water insoluble carrier.

13. The formulation of claim 12, wherein the lipoic acid is released from a water soluble or water insoluble carrier comprising polyethylene glycol, polyvinylpyrrolidone, hydroxypropylmethyl-cellulose, phosphatidylcholine, polyoxyethylene hydrogenated castor oil, hydroxypropylmethylcellulose phthalate, carboxymethylethylcellulose, or hydroxypropylmethylcellulose, ethyl cellulose, or stearic acid.

14. The formulation of claim 5, wherein the lipoic acid is released from a composition comprising a complex between an ion exchange resin and active ingredient.

* * * * *